Figure 1:
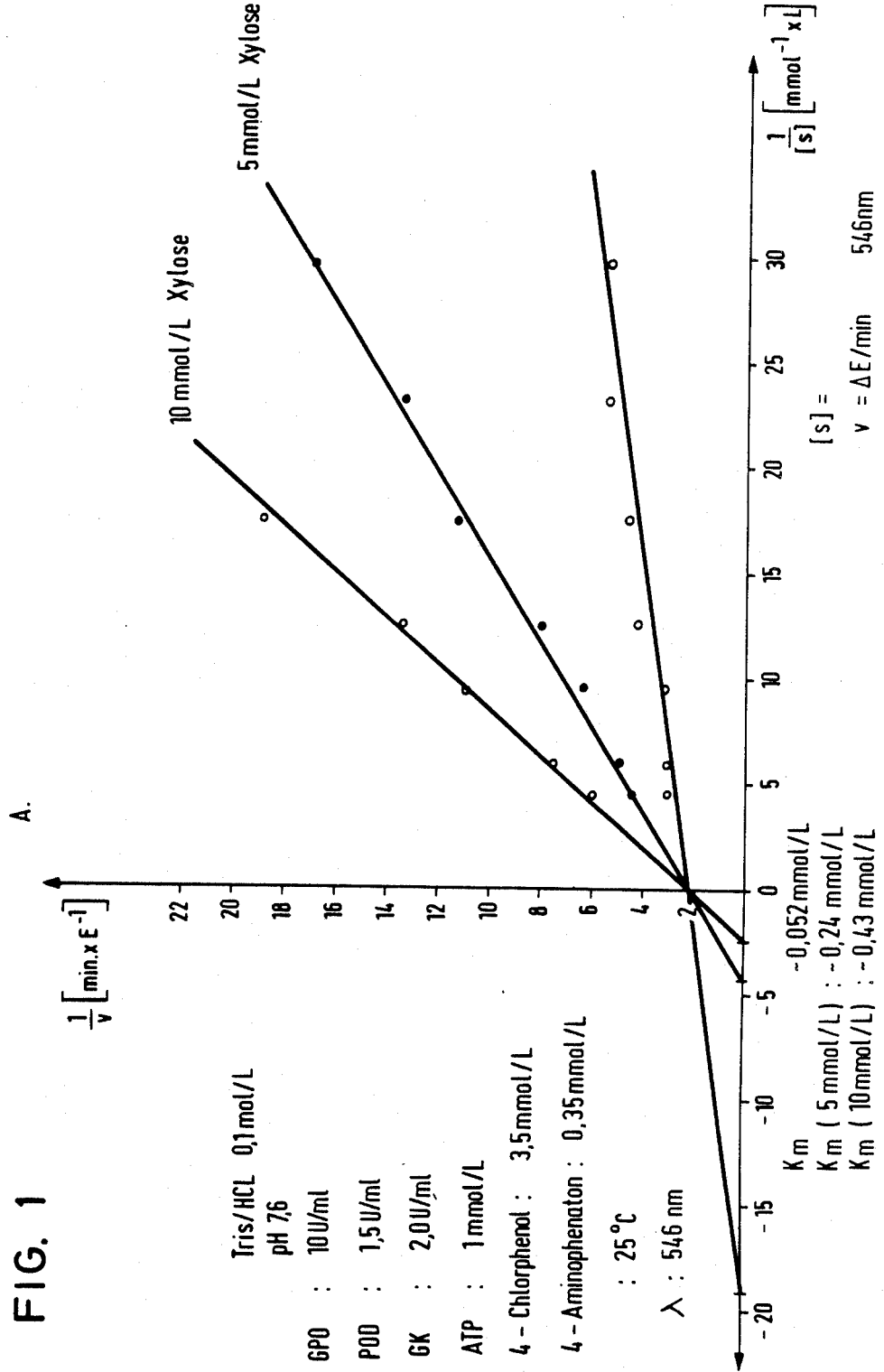

United States Patent [19]

Willnow et al.

[11] Patent Number: 4,705,749
[45] Date of Patent: Nov. 10, 1987

[54] PROCESS AND REAGENT FOR THE DETERMINATION OF GLYCEROL WITH THE USE OF GLYCEROL KINASE

[75] Inventors: Peter Willnow, Bernried; Paul Lehmann, Tutzing; Joachim Ziegenhorn, Starnberg; August W. Wahlefeld, Hohenpeissenberg, all of Fed. Rep. of Germany

[73] Assignee: Boehringer Mannheim GmbH, Mannheim-Waldhof, Fed. Rep. of Germany

[21] Appl. No.: 667,279

[22] Filed: Nov. 1, 1984

[30] Foreign Application Priority Data

Nov. 10, 1983 [DE] Fed. Rep. of Germany ....... 3340709

[51] Int. Cl.$^4$ ................ C12Q 1/48; C12Q 1/44; C12Q 1/26; C12Q 1/32; C12Q 1/28; C12N 9/99
[52] U.S. Cl. ................................... 435/15; 435/19; 435/25; 435/26; 435/28; 435/184; 435/805; 435/810
[58] Field of Search .............. 435/11, 15, 18, 19, 435/26, 28, 184, 194, 805, 810, 25

[56] References Cited

U.S. PATENT DOCUMENTS

| | | | |
|---|---|---|---|
| 3,977,944 | 8/1976 | Müller-Matthesius et al. ....... | 435/14 |
| 4,218,535 | 8/1980 | Ray ........................................ | 435/12 |
| 4,368,261 | 1/1983 | Klose et al. ............................ | 435/15 |

OTHER PUBLICATIONS

Lehninger, A. L., *Biochemistry*, 2nd edition, Worth Publishers, Inc., N.Y., (1975) pp. 250 and 258.

*Primary Examiner*—Esther M. Kepplinger
*Attorney, Agent, or Firm*—Felfe & Lynch

[57] ABSTRACT

The present invention provides a process for the determination of glycerol in free or bound form by reaction with ATP in the presence of glycerol kinase (GK) and optionally of a hydrolase with the formation of glycerol-3-phosphate and ADP and determination of one of these reaction products with the help of at least one subsequent enzymatic reaction, wherein the determination is carried out kinetically and, for this purpose, the reaction with ATP is made rate-determining for the whole reaction and this is allowed to proceed according to the pseudo-first order in that there is added a sugar of the general formula:

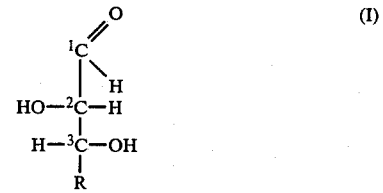

in which carbon atoms 2 and 3 have the D-threo configuration and R is a carbohydrate radical containing up to 3 carbon atoms and in which one hydroxyl group can also be replaced by a hydrogen atom.

The present invention also provides a reagent for the kinetic determination of glycerol, comprising glycerol kinase, ATP and a system for the determination of glycerol-3-phosphate or of ADP and optionally a hydrolase, wherein it additionally contains a sugar of the general formula:

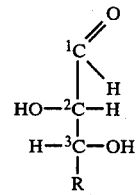

in which carbon atoms 2 and 3 have the D-threo configuration and R is a carbohydrate radical containing up to 3 carbon atoms and in which one hydroxyl group can also be replaced by a hydrogen atom.

19 Claims, 2 Drawing Figures

PROCESS AND REAGENT FOR THE DETERMINATION OF GLYCEROL WITH THE USE OF GLYCEROL KINASE

The present invention is concerned with a process and a reagent for the determination of glycerol with the use of glycerol kinase.

It is known to determine glycerol, possibly after previous liberation from its esters by chemical or enzymatic saponification, by reaction with ATP in the presence of glycerol kinase (GK), with the formation of glycerol-3-phosphate and ADP and measurement of one of these reaction products with the help of at least one subsequent enzymatic reaction (see H. U. Bergmeyer, "Methoden der enzymatischen Analyse", 3rd edition, pp. 1448 and 1872).

Because of its specificity, this enzymatic glycerol determination method has admittedly provided a considerable advance in comparision with the previously used chemical methods of determination but hitherto the process has not been suitable for a rapid and practicable kinetic carrying out thereof. Because of the low $K_M$ value of glycerol kinase, which catalyzes the most specific partial step of the reaction sequence, the reaction does not proceed according to the first or pseudo-first order in the range of concentration which is of most interest for the determination of glycerol. However, such a course of reaction is a prerequisite of a rapid, practicable kinetic method of determination which does not require a blank, which would make possible a substantial shortening of the time requirement per individual analysis in comparison with the previously necessary end point or kinetic methods. The time requirement for the previous photometric processes was thereby between 10 and 6 minutes. In the case of kinetic methods, analysis times of from 1 to 3 minutes are aimed for. The new generation of automatic analysis apparatus aims for a high sample throughput and only permits short incubation times which could not have be achieved with the previously known processes in the scope of the detection of glycerol. Consequently, the automatic analysers which are usual today cannot be fully utilized with high analysis frequencies.

Therefore, it is an object of the present invention to provide a kinetic process of determination for the glycerol kinase reaction in which this proceeds according to the pseudo-first order.

It is known that, in many cases, it is possible to achieve such a course of reaction at too low $K_M$ values of the participating enzymes by artificial increase of the $K_M$ value. From the theory of Michaelic and Menton, it follows that enzyme-catalyzed single substrate reactions then take place over a wide range of concentrations according to the first order when the Michaelis constant of the enzyme is very much greater than the maximum substrate concentration. Since the previously known glycerol kinase from various genus of micro-organisms, such as Bacillus, *Escherichia coli*, Candida, Cellulomonas, Streptomyces or yeast, have $K_M$ values (glycerol) of the order of magnitude of $10^{-4}$ to $10^{-5}$ mole/liter, here only low glycerol concentrations can be measured kinetically. It is admittedly known that, by the addition of a competitive inhibitor, the $K_M$ value of an enzyme can be artificially increased but a suitable competitive inhibitor for GK is not known.

Therefore, it is an object of the present invention to provide a process and a reagent which makes possible a kinetic determination of glycerol in the scope of a multi-step enzymatic process and which can also be used for automatic analysers of high frequency. The process is also to be capable of being carried out as a color test and to be usable on test strips.

Thus, according to the present invention, there is provided a process for the determination of glycerol in free or bound form by reaction with ATP in the presence of glycerol kinase (GK) and optionally of a hydrolase with the formation of glycerol-3-phosphate and ADP and determination of one of these reaction products with the help of at least one subsequent enzymatic reaction, wherein the determination is carried out kinetically and, for this purpose, the reaction with ATP is made rate-determining for the whole reaction and is allowed to take place according to the pseudo-first order in that there is added a sugar of the general formula:

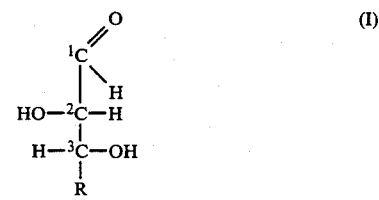

in which carbon atoms 2 and 3 have the D-threo configuration and R is a carbohydrate radical containing up to 3 carbon atoms and in which one hydroxyl group can also be replaced by a hydrogen atom.

The present invention is based upon the surprising ascertainment that sugars of general formula (I) are competitive inhibitors of GK and, therefore, are outstandingly suitable for the change of the $K_M$.

Typical examples of inhibitors which can be used according to the present invention include threose ($R=CH_2OH$), L-xylose, D-arabinose ($R=CHOH-CH_2OH$), L-fucose ($R=CHOH-CHOH-CH_3$), L-galactose and L-glucose ($R=CHOH-CHOH-CH_2OH$), L-xylose being preferably used.

In the scope of the process according to the present invention, a sugar of general formula (I) is preferably used in an amount of from 1 to 200 mMole/liter. The particular amount required depends, on the one hand, upon the $K_M$ aimed for and, on the other hand upon the amount of GK. The GK itself is generally used in amounts of from $10^2$ to $10^4$ U/liter, although smaller or larger amounts can also be considered.

The kinetic determination takes place in a known manner, at least two measurements preferably being carried out at a predetermined interval of time. The best results are thereby obtained in a pH value range of about 7.5 to about 8.5 but it is possible to deviate outside of this range depending upon the conditions given by the adjuvant enzymes.

Which adjuvant enzymes are further required depends upon which reaction product of the velocity-determining reaction is to be determined, i.e. glycerol-3-phosphate or ATP. According to a preferred embodiment of the present invention, glycerol-3-phosphate formed is converted with glycerol-3-phosphate oxidase into dihydroxyacetone phosphate and hydrogen peroxide and the latter then determined in the usual way. This embodiment of the present invention can be illustrated by the following reaction equations:

(1) triglyceride + 3H$_2$O $\xrightarrow{\text{esterase EC 3.1.1}}$ glycerol + fatty acids (2) glycerol + ATP $\xrightarrow[\text{compound of}]{\text{GK EC 2.7.1.30}}$ general formula (I)

glycerol—3-phosphate + ADP (3) glycerol—3-phosphate + O$_2$ $\xrightarrow{\text{GPO}}$ dihydroxyacetone phosphate + H$_2$O$_2$ As the above equations show, hydrogen peroxide is hereby formed and this can be converted, for example, with peroxidase in the presence of phenol and 4-aminoantipyrine in GOOD buffer, into a directly measurable coloured material.

Since the above reaction (3) takes place with the consumption of oxygen, instead of hydrogen peroxide, there can also be measured the dihydroxyacetone phosphate or the consumption of oxygen.

Alternatively, the ADP formed can be measured. This can take place, for example, by replacing the above reaction according to equation (3) by reactions according to the following equations:

(4) ADP + PEP $\xrightarrow{\text{PK}}$ pyruvate + ATP (5) pyruvate + NADH $\xrightarrow{\text{LDH}}$ lactate + NAD$^+$ The NADH decrease can hereby be monitored directly in ultra-violet light.

In the case of this determination, ADP is reacted with phosphoenol pyruvate (PEP) in the presence of pyruvate kinase (PK) to give pyruvate which, in turn, is reacted with NADH in the presence of lactate dehydrogenase (LDH) to give lactate and NAD$^+$.

According to a further embodiment of the present invention, glycerol-3-phosphate formed is determined by reaction with NAD$^+$ in the presence of glycerol phosphate dehydrogenase, with the formation of dihydroxyacetone phosphate and NADH. The latter is determined either directly in ultra-violet light or by reaction with a tetrazolium salt in the presence of diaphorase. In the latter case, the formazane coloured material formed is measured.

This reaction can be illustrated by the following reaction equations (6) and (7) which are used instead of the reaction according to equation (3):

(6) NAD$^+$ + glycerol—3-phosphate $\xrightarrow{\text{glycerol phosphate dehydrogenase}}$ NADH + dihydroxyacetone phosphate (7) NADH + tetrazolium salt $\xrightarrow{\text{diaphorase}}$ NAD$^+$ + formazane The process according to the present invention can advantageously be carried out in the presence of a non-ionic detergent and optionally additionally of a detergent of the cholic acid group of compounds.

There are no limitations with regard to the source of the glycerol kinase used. Typical examples of glycerol kinases which can be used in the scope of the present invention include the enzymes from *Bacillus stearothermophilus, Escherichia coli, Candida mycoderma, Streptomyces canus,* Cellulomonas sp. and yeast. At the moment, the enzyme is not commercially available from other sources. The enzyme from *Bacillus stearothermophilus* is preferably used.

The present invention also provides a reagent for the kinetic determination of glycerol, which comprises glycerol kinase, ATP and a system for the determination of glycerol-3-phosphate or of ADP and optionally a hydrolase, which reagent additionally contains a sugar of the general formula:

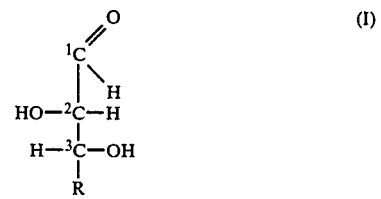

in which carbon atoms 2 and 3 have the D-threo configuration and R is a carbohydrate radical with up to 3 carbon atoms and in which one hydroxyl group can also be replaced by a hydrogen atom.

The composition of the reagent according to the present invention is qualitatively determined by the particular system employed for the determination of the glycerol-3-phosphate or ADP. For the quantitative composition, the statements made above with regard to the process apply in the same manner. Thus, the reagent preferably contains 1 to 200 mMole/liter of a compound of general formula (I), the preferred compound of general formula (I) being L-xylose.

The system for the determination of glycerol-3-phosphate preferably consists either of glycerol phosphate oxidase and a system for the determination of hydrogen peroxide or of dihydroxyacetone phosphate or consists of glycerol phosphate dehydrogenase, NAD$^+$, tetrazolium salt and diaphorase.

The system for the determination of hydrogen peroxide preferably consists of 4-aminoantipyrine, phenol or a phenol derivative, buffer and a detergent.

If the reagent according to the present invention contains a system for the determination of ADP, then the latter preferably consists of phosphoenol pyruvate, pyruvate kinase, NADH and lactate dehydrogenase.

In an especially preferred composition, the reagent according to the present invention comprises, according to reaction equations (1) to (3):

$10^2$ to $10^4$ U/liter glycerol kinase,
$10^2$ to $10^4$ U/liter glycerol phosphate oxidase,
$10^3$ to $2\times 10^4$ U/liter cholesterol esterase,
$10^2$ to $10^4$ U/liter peroxidase,
1 to 20 mMole/liter L-xylose,
0.1 to 1 mMole/liter 4-aminoantipyrine,
1 to 10 mMol/liter phenol or phenol derivative,
1 to 20 g./liter non-ionic detergent,
0 to 15 mMole/liter detergent of the cholic acid group,
50 to 200 mMole/liter buffer (pH 7.5 to 8.5).

As buffer substances, there can be used all buffers which are effective in the given pH range, GOOD buffer being preferred.

The process according to the present invention can be carried out in conventional analysis apparatus and automatic analysers, as is indicated in more detail in the following specific Examples. The reagent can also be present impregnated in a solid carrier, for example in paper strips. In the latter case, the colour formation can also be determined kinetically and quantitatively.

The effectiveness of the inhibitor used according to the present invention can be seen from the accompanying drawings, in which:

FIG. 1 is a graphic representation of the measured reaction velocities without competitive inhibiting material and with various concentrations of a compound of general formula (I) (L-xylose), using the enzyme from *Bacillus stearothermophilus*. The reagent composition used was as follows:

2.0 U/ml. GK,
1.5 U/ml. POD,
10 U/ml. GPO,
1 mMole/liter ATP,
3.5 mMole/liter 4-chlorophenol,
0.35 mMole/liter 4-aminoantipyrine,
0.1 mole/liter tris/HCl buffer (pH 7.6)
temperature 25° C.; measurement wavelength 546 nm. From the curves, there is given a $K_M$ without inhibitor $\approx 0.052$ mMole/liter. With 5 mMole/liter of inhibitor, the $K_M$ was 0.24 mMole/liter and with 10 mMole/liter of inhibitor was $\approx 0.43$ mMole/liter.

Figure 2:
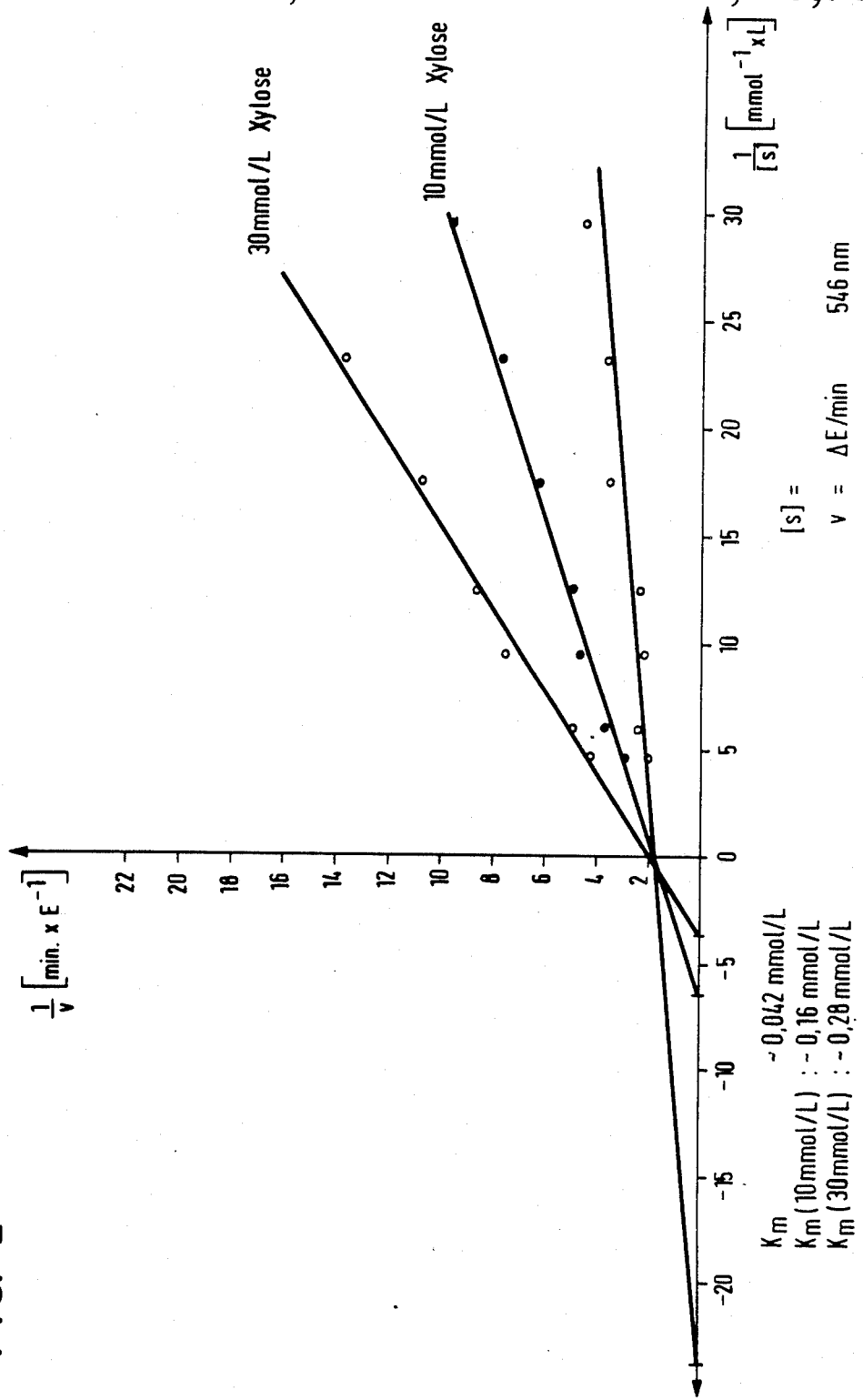

FIG. 2 corresponds to FIG. 1 except that the enzyme from *Escherichia coli* was used. The $K_M$ without inhibitor was found to be about 0.042 mMole/liter, with 10 mMole/liter inhibitor to be 0.16 mMole/liter and with 30 mMole/liter inhibitor to be 0.28 mMole/liter.

The process and reagent of the present invention can be used for the measurement of glycerol or of triglycerides in serum or plasma, for example heparin or EDTA plasma can be used.

The following Examples are given for the purpose of illustrating the present invention:

EXAMPLE 1

Reagent used:

| tris/HCl buffer | 0.15 mole/litre, pH 7.6 |
| --- | --- |
| magnesium sulphate heptahydrate | 17.5 mMole/litre |
| EDTA disodium salt | 10 mMole/litre |
| 4-chlorophenol | 3.5 mMole/litre |
| sodium cholate | 0.15% |
| detergent | 0.12% |
| ATP | $\geq$ 0.5 mMole/litre |
| 4-aminoantipyrine | = 0.35 mMole/litre |
| esterase | $\geq$ 3 U/litre |
| glycerol phosphate oxidase | $\geq$ 2.5 U/ml. |
| glycerol kinase | $\geq$ 0.2 U/ml. |
| peroxidase | $\geq$ 0.15 U/ml. |

Determination batch:

| wavelength | Hg 546 spectrophotometer: 500 nm |
| --- | --- |
| cuvette | 1 cm. layer thickness |
| incubation temperature | 20 to 25° C. or 37° C. |

One blank and one standard suffice for each series of measurements.

| Pipette into reagent glasses | | | |
| --- | --- | --- | --- |
| | blank | sample | standard |
| sample material | — | 0.02 ml. | — |
| standard | — | — | 0.02 ml. |
| reagent solution | 2.00 ml. | 2.00 ml. | 2.00 ml. | mix, incubate blank, sample and standard for 10 minutes at 20 to 25° C. or 37° C. Within 30 minutes, measure extinction of the sample against the blank.

The dilution limit is 1000 mg./dl. or 11.4 mMole/liter. In the case of higher concentrations, dilute the sample 1+5 with 0.9% aqueous sodium chloride solution and repeat the determination: result ×6.

As standard, there is used a glycerol solution corresponding to 200 mg./dl. triglycerides.

Calculation:
Evaluation via the standard:

$$c \text{ [mg/dl]} = \frac{E \text{ sample}}{E \text{ standard}} \times 200$$

Evaluations via factor:
The concentration of the triglycerides in the sample is calculated according to:

| measurement wavelength | c [mg./dl.] | c [mMole/litre] |
| --- | --- | --- |
| Hg 546 nm | 1040 × $E_{sample}$ | 11.9 × $E_{sample}$ |
| 500 nm | 760 × $E_{sample}$ | 8.66 × $E_{sample}$ |

EXAMPLES 2 TO 7

Comparative investigation of various inhibitors according to the present invention with GK of varying origin:

Reagent composition:

| tris/HCl | 0.1 mole/litre, pH 7.6 |
| --- | --- |
| glycerol phosphate oxidase | 10 U/ml. |
| peroxidase | 1.5 U/ml. |
| glycerol kinase | 2.0 U/ml. |
| magnesium sulphate heptahydrate | 17.5 mMole/litre |
| inhibitor | see Table |
| 4-chlorophenol | 3.5 mMole/litre |
| 4-aminoantipyrine | 0.35 mMole/litre |
| ATP | 1 mMole/litre |

Sample: aqueous glycerol solution 6 mMole/liter
sample/reagent ratio 1:100 (20 μl./2 ml.)
temperature: 25° C.
measurement wavelength 546 nm. ($\Delta E$/min. in each case read off from the linear region)

The results obtained with L-xylose, L-fucose and L-arabinose in the case of the use of enzyme from *Bacillus stearothermophilus* and *Escherichia coli* are given in the following Tables 1 and 2.

TABLE 1

| GK from *Bacillus stearothermophilus* | | | | | |
| --- | --- | --- | --- | --- | --- |
| L-xylose [mMol/l] | $\Delta E$/min | L-fucose [mMol/l] | $\Delta E$/min | D-arabinose [mMol/l] | $\Delta E$/min |
| — | 0.515 | — | 0.522 | — | 0.509 |
| 2 | 0.320 | 10 | 0.230 | 10 | 0.426 |
| 5 | 0.188 | 20 | 0.153 | 20 | 0.349 |
| 10 | 0.105 | 50 | 0.077 | 50 | 0.249 |
| 20 | 0.062 | 100 | 0.039 | 100 | 0.121 |

TABLE 2

| | GK from *Escherichia coli* | | | | |
|---|---|---|---|---|---|
| L-xylose [mMol/l] | ΔE/min | L-fucose [mMol/l] | ΔE/min | D-arabinose [mMol/l] | ΔE/min |
| — | 0.420 | — | 0.441 | — | 0.435 |
| 5 | 0.228 | 20 | 0.352 | 20 | 0.363 |
| 10 | 0.169 | 50 | 0.286 | 50 | 0.302 |
| 20 | 0.118 | 100 | 0.209 | 100 | 0.231 |
| 50 | 0.072 | 150 | 0.142 | 150 | 0.167 |

We claim:

1. In a process for the determination of glycerol by reaction with ATP in the presence of glycerol kinase (GK) with the formation of glycerol-3-phosphate and ADP followed by a measuring step wherein glycerol-3-phosphate or ADP is determined by at least one subsequent enzymatic reaction followed by a measurement of the subsequent enzymatic reaction product, the improvement comprising:
competitively inhibiting the glycerol kinase (GK) to render the reaction with ATP rate-determining for the whole reaction and pseudo-first order, by adding, as an inhibitor, a sugar of the formula:

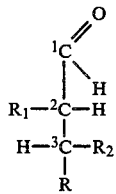

in which carbon atoms 2 and 3 have the D-threo configuration, R is a carbohydrate radical containing up to 3 carbon atoms and $R_1$ and $R_2$ are hydroxyl or one of $R_1$ and $R_2$ is hydroxyl and the other is hydrogen.

2. The process of claim 1, wherein 1 to 200 mMole/liter of the inhibitor is added.

3. The process of claim 1, wherein the inhibitor is L-xylose.

4. The process of claim 1 wherein from $10^2$ to $10^4$ U/liter of glycerol kinase are added.

5. The process of claim 1, wherein at least two measurements are carried out at a predetermined time interval.

6. The process of claim 1, wherein the reaction with ATP is carried out in buffered solution at a pH value of from 7.5 to 8.5.

7. Process according to claim 1 wherein the glycerol-3-phosphate is measured in the measuring step by converting the glycerol-3-phosphate with glycerol-3-phosphate oxidase into dihydroxyacetone phosphate and measuring the amount of hydrogen peroxide formed.

8. The process of claim 7, wherein the hydrogen peroxide formed is measured by adding 4-amino-antipyrine, phenol and peroxidase.

9. The process of claim 1, wherein the ADP is measured in the measuring step by reacting the ADP with phosphenol pyruvate in the presence of pyruvate kinase to form pyruvate, reacting the pyruvate with NADH in the presence of lactate dehydrogenase to form lactate and $NAD^+$, and measuring the NADH decrease.

10. The process of claim 1 wherein the glycerol-3-phosphate is measured in the measuring step by reacting the glycerol-3-phosphate with $NAD^+$ in the presence of glycerol phosphate dehydrogenase to form dihydroxyacetone phosphate and NADH thereafter oxidizing the NADH with tetrazolium salt in the presence of diaphorase to form a formazane colored material which is measured.

11. In a reagent for the determination of glycerol, comprising glycerol kinase, ATP and a system for the determination of glycerol-3-phosphate or of ADP the improvement comprising a glycerol kinase competitive inhibitor in an amount effective to competitively inhibit said glycerol kinase comprising a sugar of the formula:

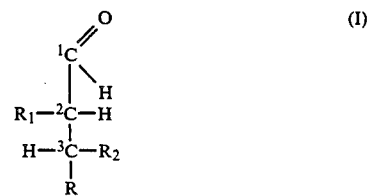

in which carbon atoms 2 and 3 have the D-threo-configuration, R is a carbohydrate radical containing up to 3 carbon atoms and $R_1$ and $R_2$ are hydroxyl or one of $R_1$ and $R_2$ is hydroxyl and the other is hydrogen.

12. The reagent of claim 11 wherein it contains 1 to 200 mMole/liter of said sugar.

13. The reagent of claim 12 wherein said sugar is L-xylose.

14. The reagent of claim 11, wherein it contains the system determination of glycerol-3-phosphate comprising glycerol phosphate oxidase and a system for the determination of hydrogen peroxide or of dihydroxyacetone phosphate.

15. The reagent of claim 14, wherein it contains the system for the determination of hydrogen peroxide comprising 4-aminoantipyrine, phenol or a derivative thereof, buffer and a detergent.

16. The reagent of claim 11, wherein it contains the system for determination of glycerol-3-phosphate consisting of glycerol phosphate dehydrogenase, $NAD^+$, tetrazolium salt and diaphorase.

17. The reagent of claim 11, wherein it contains a system for the determination of ADP consisting of phosphoenol pyruvate, pyruvate kinase, NADH and lactate dehydrogenase.

18. The reagent of claim 11 containing:
$10^2$ to $10^4$ U/liter glycerol kinase,
$10^2$ to $10^4$ U/liter glycerol phosphate oxidsase,
$10^3$ to $2\times10^4$ U/liter cholesterol esterase,
$10^2$ to $10^4$ U/liter peroxidase,
1 to 20 mMole/liter L-xylose,
0.1 to 1 mMole/liter 4-aminoantipyrine,
1 to 10 mMole/liter phenol or phenol derivative,
1 to 20 g./liter non-ionic detergent,
0 to 15 mMole/liter detergent of the cholic acid group,
50 to 200 mMole/liter buffer (pH 7.5 to 8.5).

19. The reagent of claim 11 impregnated on to a solid carrier.

* * * * *

UNITED STATES PATENT AND TRADEMARK OFFICE
CERTIFICATE OF CORRECTION

PATENT NO. : 4,705,749
DATED : November 10, 1987
INVENTOR(S) : Peter Willnow

It is certified that error appears in the above-identified patent and that said Letters Patent is hereby corrected as shown below:

Column 5, line 65: after line 65 insert -- measurement against blank (extinction increase) --.

Column 6, line 56: first word delete "L-arabinose" and insert -- D-arabinose --.

Column 7, line 62: first word, delete "phosphenol" and insert -- phosphoenol --.

Signed and Sealed this

Twelfth Day of July, 1988

Attest:

DONALD J. QUIGG

Attesting Officer

Commissioner of Patents and Trademarks